(12) United States Patent
Zhang et al.

(10) Patent No.: US 12,226,846 B2
(45) Date of Patent: Feb. 18, 2025

(54) STERILE SEALING APPARATUS (71) Applicant: SAINT-GOBAIN PERFORMANCE PLASTICS CORPORATION, Solon, OH (US)

(72) Inventors: Jianfeng Zhang, Shrewsbury, MA (US); Rachel Z. Pytel, Newton, MA (US); Jian L. Ding, Stow, MA (US); Anthony P. Pagliaro, Lansdale, PA (US); Clemens E. Zoellner, Bay City, MI (US)

(73) Assignee: SAINT-GOBAIN PERFORMANCE PLASTICS CORPORATION, Solon, OH (US)

( * ) Notice: Subject to any disclaimer, the term of this patent is extended or adjusted under 35 U.S.C. 154(b) by 173 days.

(21) Appl. No.: 17/182,669

(22) Filed: Feb. 23, 2021

(65) Prior Publication Data

US 2021/0291291 A1   Sep. 23, 2021

Related U.S. Application Data

(60) Provisional application No. 62/992,298, filed on Mar. 20, 2020.

(51) Int. Cl.
*B23K 10/02* (2006.01)
*B29C 65/20* (2006.01)
(Continued)

(52) U.S. Cl.
CPC .......... *B23K 10/02* (2013.01); *B29C 65/2076* (2013.01); *H05H 1/26* (2013.01); *B23K 2103/42* (2018.08); *H05H 2277/10* (2013.01)

(58) Field of Classification Search
CPC .......................... B23K 10/02; B23K 2101/06; B23K 26/0093; B23K 26/38; B23K 2103/42;
(Continued)

(56) References Cited

U.S. PATENT DOCUMENTS 3,555,231 A   1/1971   Laurentie et al.
4,039,798 A * 8/1977   Lythall .................. B23K 9/325
                                             219/121.45
(Continued)

FOREIGN PATENT DOCUMENTS

CA   2116433 C   12/2004
CA   2461223 C    5/2013
(Continued)

OTHER PUBLICATIONS

International Search Report and Written Opinion for PCT/US2021/019197, mailed Jun. 11, 2021, 9 pages.
(Continued)

*Primary Examiner* — Helena Kosanovic
*Assistant Examiner* — Thao Uyen Tran-Le
(74) *Attorney, Agent, or Firm* — Abel Schillinger, LLP; Chi Suk Kim (57) ABSTRACT

Systems and methods are disclosed that include an operation chamber, a plasma generator having at least one plasma head disposed within the operation chamber and in proximity to a profile formed by cutting a piece of tubing, and a mechanical motion module. The plasma generator generates a plasma treatment and applies the plasma treatment via the at least one plasma head to the profile to activate material on an end surface of the profile, within a lumen of the profile, or a combination thereof. Once the material of the profile is activated by the plasma treatment, the mechanical motion module manipulates the profile to close the lumen of the profile to aseptically seal the profile.

18 Claims, 5 Drawing Sheets

(51) Int. Cl.
  *H05H 1/26* (2006.01)
  *B23K 103/00* (2006.01)
(58) Field of Classification Search
  CPC ... B29C 66/43; B29C 65/2076; B29C 66/832;
    B29C 66/71; B29C 66/857; B29C 57/10;
    B29C 66/028; B29C 66/1122; B29C
    66/137; B29C 66/121; B29C 66/73921;
    B29C 66/73941; B29C 65/1432; H05H
    1/26; H05H 2277/10; A61M 39/18;
    A61M 2205/502; A61M 2207/10; A61M
    39/20; A61M 39/146; A61M 39/14; B29L
    2023/007; B29K 2021/003; B29K
    2025/06; B29K 2067/00; B29K 2083/00;
    B29K 2077/00; B29K 2023/00; B29K
    2033/00; B29K 2055/00; B29K 2007/00
  See application file for complete search history.

(56) References Cited

U.S. PATENT DOCUMENTS

| | | | |
|---|---|---|---|
| 4,516,971 A * | 5/1985 | Spencer | B29C 66/5221 |
| | | | 604/905 |
| RE32,056 E | 12/1985 | Granzow et al. | |
| 4,610,670 A | 9/1986 | Spencer | |
| 4,793,880 A | 12/1988 | Shaposka et al. | |
| 4,913,756 A | 4/1990 | Shaposka et al. | |
| 5,801,489 A * | 9/1998 | Chism, Jr. | H05H 1/36 |
| | | | 219/121.36 |
| 5,858,016 A | 1/1999 | Bacehowski et al. | |
| 6,000,436 A | 12/1999 | Auvil et al. | |
| 6,228,204 B1 | 5/2001 | Reinhardt et al. | |
| 6,270,860 B1 | 8/2001 | Nakata et al. | |
| 6,299,596 B1 * | 10/2001 | Ding | C08J 7/123 |
| | | | 427/535 |
| 6,468,482 B1 | 10/2002 | Frieze et al. | |
| 6,664,499 B1 * | 12/2003 | Brink | B23K 26/032 |
| | | | 219/121.67 |
| 7,226,649 B2 | 6/2007 | Shang et al. | |
| 7,329,608 B2 | 2/2008 | Babayan et al. | |
| 7,442,271 B2 | 10/2008 | Asmussen et al. | |
| 7,754,816 B2 | 7/2010 | Snider | |
| 8,424,923 B2 | 4/2013 | Inman, Jr. et al. | |
| 8,613,367 B2 | 12/2013 | Ou et al. | |
| 8,975,163 B1 * | 3/2015 | Lei | H01L 21/6836 |
| | | | 257/E21.602 |
| 9,550,015 B2 | 1/2017 | Gray | |
| 10,081,135 B2 | 9/2018 | Patil et al. | |
| 10,195,416 B2 | 2/2019 | Gebauer et al. | |
| 10,304,977 B1 * | 5/2019 | Okandan | H01L 31/054 |
| 10,500,794 B2 | 12/2019 | Takemoto et al. | |
| 10,550,966 B2 | 2/2020 | Blomberg | |
| 10,794,525 B2 | 10/2020 | Pennock et al. | |
| 11,441,716 B2 | 9/2022 | Tamaribuchi et al. | |
| 2002/0006353 A1 | 1/2002 | Bilstad et al. | |
| 2002/0100540 A1 | 8/2002 | Savitski et al. | |
| 2002/0172780 A1 * | 11/2002 | Halverson | H01J 37/32192 |
| | | | 118/723 MR |
| 2003/0015816 A1 | 1/2003 | Rapacki et al. | |
| 2003/0102293 A1 | 6/2003 | Therond | |
| 2003/0148555 A1 * | 8/2003 | Akita | G06K 19/07745 |
| | | | 257/730 |
| 2003/0195609 A1 | 10/2003 | Berenstein et al. | |
| 2003/0196418 A1 | 10/2003 | O'Brien et al. | |
| 2004/0016504 A1 | 1/2004 | Mitarai | |
| 2004/0067705 A1 | 4/2004 | Ton-That et al. | |
| 2004/0144492 A1 | 7/2004 | Ikeda et al. | |
| 2005/0017505 A1 | 1/2005 | Thilly | |
| 2005/0090797 A1 | 4/2005 | Almasian et al. | |
| 2005/0252608 A1 | 11/2005 | MacDonald | |
| 2006/0070677 A1 * | 4/2006 | Inoue | B29C 59/103 |
| | | | 138/109 |
| 2006/0081567 A1 | 4/2006 | Dougherty, Sr. et al. | |
| 2006/0110282 A1 | 5/2006 | Bilstad et al. | |
| 2006/0191623 A1 | 8/2006 | Lutz et al. | |
| 2006/0284417 A1 | 12/2006 | Brown | |
| 2007/0118225 A1 * | 5/2007 | Hestad | A61F 2/442 |
| | | | 623/17.16 |
| 2007/0142960 A1 | 6/2007 | Bollinger et al. | |
| 2008/0009833 A1 | 1/2008 | Corbin et al. | |
| 2008/0202669 A1 | 8/2008 | Zemmouri et al. | |
| 2008/0257604 A1 | 10/2008 | Becker et al. | |
| 2008/0277926 A1 | 11/2008 | Inman, Jr. et al. | |
| 2009/0197016 A1 * | 8/2009 | Inoue | F16L 33/34 |
| | | | 427/569 |
| 2011/0171480 A1 | 7/2011 | Mori et al. | |
| 2011/0220290 A1 | 9/2011 | Hlavinka et al. | |
| 2013/0158189 A1 * | 6/2013 | Reniers | C09D 127/04 |
| | | | 427/575 |
| 2014/0004503 A1 * | 1/2014 | Cima | G01N 33/5767 |
| | | | 435/7.1 |
| 2014/0077488 A1 | 3/2014 | Wegener et al. | |
| 2014/0197141 A1 | 7/2014 | Dorey et al. | |
| 2014/0263202 A1 | 9/2014 | Partridge | |
| 2014/0283940 A1 | 9/2014 | Bourgeois et al. | |
| 2014/0314818 A1 * | 10/2014 | Giare-Patel | A61L 29/106 |
| | | | 514/635 |
| 2016/0109052 A1 | 4/2016 | Yodogawa et al. | |
| 2016/0146392 A1 | 5/2016 | Pennock et al. | |
| 2016/0200038 A1 | 7/2016 | Gagne et al. | |
| 2016/0235962 A1 | 8/2016 | Gebauer | |
| 2017/0107345 A1 | 4/2017 | Kon et al. | |
| 2017/0141001 A1 | 5/2017 | Sakiyama et al. | |
| 2017/0221856 A1 * | 8/2017 | Yamauchi | H01L 21/67092 |
| 2017/0326584 A1 | 11/2017 | Ennon et al. | |
| 2018/0161554 A1 | 6/2018 | Takemoto | |
| 2018/0320026 A1 | 11/2018 | De Beer | |
| 2019/0048230 A1 | 2/2019 | Hahnel | |
| 2019/0105849 A1 | 4/2019 | Schwalm et al. | |
| 2019/0134243 A1 * | 5/2019 | Nelson | H05H 1/2406 |
| 2019/0284443 A1 | 9/2019 | Sherman et al. | |
| 2019/0313863 A1 * | 10/2019 | Laundre | A47K 13/12 |
| 2020/0071199 A1 * | 3/2020 | Lewis, III | H05H 1/48 |
| 2021/0001563 A1 | 1/2021 | Zhang et al. | |
| 2021/0001566 A1 | 1/2021 | Zhang et al. | |
| 2021/0076480 A1 | 3/2021 | Ikedo et al. | |
| 2021/0178506 A1 | 6/2021 | Zhang et al. | |
| 2021/0199226 A1 | 7/2021 | Zhang et al. | |
| 2021/0394459 A1 | 12/2021 | Zhang et al. | |

FOREIGN PATENT DOCUMENTS

| | | |
|---|---|---|
| CN | 1695844 A | 11/2005 |
| CN | 101579757 A | 11/2009 |
| CN | 102061440 A | 5/2011 |
| CN | 102159868 A | 8/2011 |
| CN | 105065804 A | 11/2015 |
| CN | 106795343 A | 5/2017 |
| CN | 206140944 U | 5/2017 |
| CN | 108127239 A | 6/2018 |
| DE | 102011010905 A1 | 8/2012 |
| DE | 102012004385 A1 | 9/2013 |
| DE | 102016003862 A | 12/2017 |
| EP | 0064288 A1 | 11/1982 |
| EP | 0479592 A2 | 4/1992 |
| EP | 1445209 B1 | 5/2008 |
| EP | 1656414 B1 | 10/2013 |
| FR | 2793178 A1 | 11/2000 |
| JP | H05456 A | 1/1993 |
| JP | 5042203 A | 2/1993 |
| JP | 6155582 A | 6/1994 |
| JP | 7251456 A | 10/1995 |
| JP | H0861581 A | 3/1996 |
| JP | H0955287 A | 2/1997 |
| JP | H09135881 A | 5/1997 |
| JP | 2000279509 A | 10/2000 |
| JP | 2006124665 A | 5/2006 |
| JP | 2009028922 A | 2/2009 |
| JP | WO2008090701 A1 | 5/2010 |
| JP | 20131322822 A | 7/2013 |
| JP | 2018015904 A1 | 2/2018 |

(56) References Cited

FOREIGN PATENT DOCUMENTS

| | | |
|---|---|---|
| JP | 2019052716 A | 4/2019 |
| KR | 20030043478 A | 6/2003 |
| KR | 20150054280 A | 5/2015 |
| KR | 101708024 B1 | 2/2017 |
| KR | 20190117741 A | 10/2019 |
| TW | 201510402 A | 3/2015 |
| WO | 200062820 A2 | 10/2000 |
| WO | 2015075040 A1 | 5/2015 |
| WO | 2016109805 A1 | 7/2016 |
| WO | 2016168754 A1 | 10/2016 |
| WO | WO-2018146880 A1 * | 8/2018 |
| WO | 2019130223 A1 | 7/2019 |
| WO | 2021003243 A1 | 1/2021 |
| WO | 2021003244 A1 | 1/2021 |
| WO | 2021118780 A1 | 6/2021 |
| WO | 2021133677 A1 | 7/2021 |
| WO | 2022094599 A1 | 5/2022 |

OTHER PUBLICATIONS

International Search Report and Written Opinion for PCT/US2020/040455, mailed Oct. 22, 2020, 10 pages.
International Search Report and Written Opinion for PCT/US2020/040454, mailed Oct. 15, 2020, 11 pages.
International Search Report and Written Opinion for PCT US2020/061198, mailed Mar. 12, 2021, 9 pages.
Kinney, Shawn D. et al., Thermoplastic Tubing Welders and Sealers: Forging the Future of Disposable Technologies in the Biopharmaceutical Industry, BioProcess International, May 2007, pp. 52-61.
TSCD-Q Sterile Tubing Welder, Discover Polyurethane Tubing Connections based on Proven Terumo BCT Technology, Terumo BCT, Inc., 2014, 6 pages.
SCD IIB, Sterile Tubing Welder, Experience Fast, Easy, Reliable Welds, Terumo BCT, Inc., 2014, 6 pages.
CPC, Comparison Guide: Tube Welders and Aseptic Connectors, Technical Guide 7009, Colder Products Company, 2018, 3 pages.
Annunziata, Marco et al., "Bacterial inactivation/sterilization by argon plasma treatment on contaminated titanium implant surfaces: In vitro study ," Med Oral Patol Oral Cir Bucal. (2015), doi: 10.4317/medoral.20845, 4 pages.
International Search Report and Written Opinion for PCT/US2021/037442, mailed Oct. 7, 2021, 9 pages.
International Search Report and Written Opinion for PCT/US2020/066066, mailed Apr. 7, 2021, 10 pages.
CJan Fluid Technology, 2017, "The Differences Between Silicone and PVC", https://web.archive.org/web/20170922114948/http://www.cjanfluid.com/blog/the-differences-between-silicone-and-pvs.html, 3 pages.
Ageorges et al., "Advances in fusion bonding techniques for joining thermoplastic matrix composites: a review", dated Oct. 25, 2000, Composites: Part A, 32, Elsevier.com, pp. 839-857 (Year: 2000).
Masuzawa et al., "Ultrasonic Welding of Plastic Pipes Using Torsional Vibration", Japanese Journal of Applied Physics, vol. 37, Part 1, No. 5B, pp. 3007-3008 (Year: 1997).
PVC Pipe Industry News, "Top 10 Benefits of PVC Pipes", dated Jan. 30, 2015, <https://www.thinkpipesthinkpvc.com.au/about-us/latest-news/entry/top-10-benefits-of-pvc-pipes>, pp. 1-4 (Year: 2015).
Medical Design Briefs, "Why is Silicone the Material of Choice for Healthcare Tubing?", dated Nov. 1, 2018, <https://www.medicaldesignbriefs.com/component/content/article/mdb/pub/features/articles/33244>, pp. 1-7, (Year: 2018).
Sgobba, Stefano, "Vacuum for Accelerators: Introduction to Materials and Properties", Proceedings of the 2017 CERN—Accelerator—School course on Vacuum for Particle Accelerators, Jun. 2020, doi.org/10.48550/arXiv.2006.02212.

* cited by examiner

FIG. 5

STERILE SEALING APPARATUS

CROSS-REFERENCE TO RELATED APPLICATIONS

This application claims priority under 35 U.S.C. § 119(e) to U.S. Provisional Application No. 62/992,298, entitled "STERILE SEALING APPARATUS," by Jianfeng ZHANG et al., filed on Mar. 20, 2020, the disclosure of which is assigned to the current assignee hereof and incorporated herein by reference in its entirety for all purposes.

BACKGROUND OF THE INVENTION

Sterile sealing of tubing may be useful in a variety of industries, including the medical industry and the pharmaceutical industry. Thermoplastic and thermoset elastomers are often used in such applications since these elastomers are non-toxic, flexible, thermally stable, have low chemical reactivity, and can be produced in a variety of sizes. In many instances, it is desirable to seal a lumen of a profile (e.g., tube, hose, or other fluid vessel having a lumen through which a fluid may be carried, pumped, or otherwise transported) to prevent the flow of a fluid or gas therethrough. Unfortunately, traditional sealing apparatuses that use high temperature methods cannot effectively seal profiles formed from thermoset elastomers, such as silicone elastomers. Further, sealing such materials also presents challenges in maintaining sterility at the connection.

SUMMARY

The present disclosure relates generally to a sealing apparatus and methods for applying a plasma treatment to an end surface and/or at least partially within a lumen of a profile, preferably in a sterile environment, to activate material on the end surface and/or within the lumen of the profile, and manipulating the profile to close the lumen of the profile to aseptically seal the lumen of the profile.

BRIEF DESCRIPTION OF THE DRAWINGS

So that the manner in which the features and advantages of the embodiments are attained and can be understood in more detail, a more particular description may be had by reference to the embodiments thereof that are illustrated in the appended drawings. However, the drawings illustrate only some embodiments and therefore are not to be considered limiting in scope as there may be other equally effective embodiments.

The use of the same reference symbols in different drawings indicates similar or identical items.

DETAILED DESCRIPTION

Figure 1:
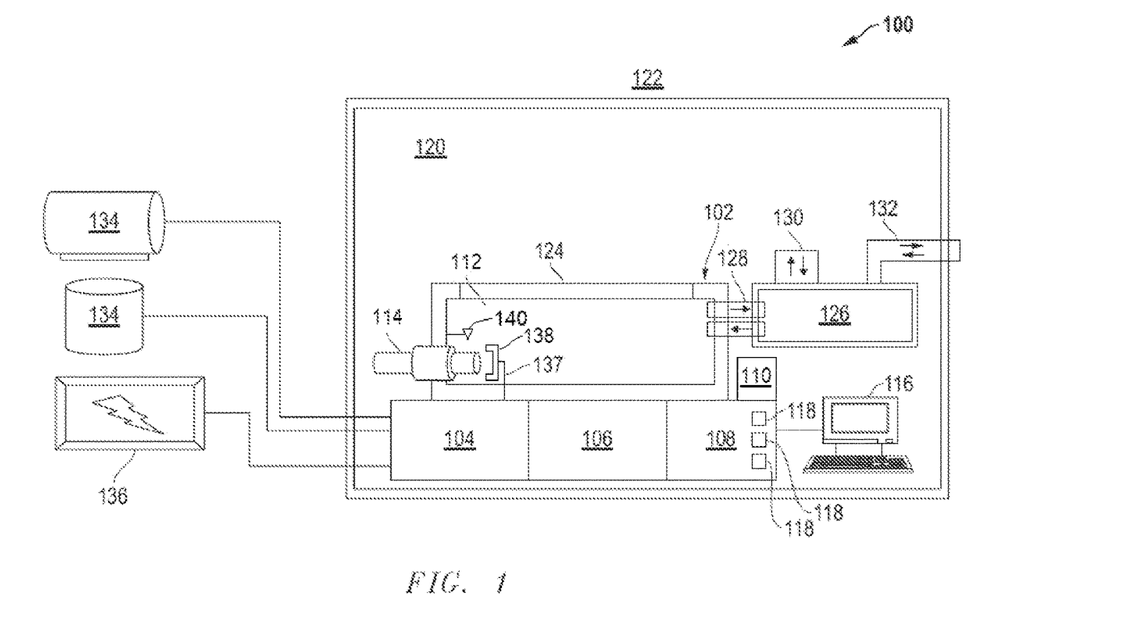
FIG. 1 is a schematic of a sterile sealing apparatus according to an embodiment of the disclosure.

FIG. 1 shows a schematic of a sterile sealing apparatus 100 according to an embodiment of the disclosure. Most generally, the sterile sealing apparatus 100 may be configured to aseptically seal a profile 114 (e.g., tube, hose, or other fluid vessel having a lumen through which a fluid may be carried, pumped, or otherwise transported) in a sterile environment. The sealing of the profile 114 may be accomplished by applying a surface activation treatment to an end surface and/or at least partially within the lumen of the profile 114, preferably in a sterile environment, to activate material on the end surface and/or within the lumen of the profile 114, and manipulating the profile 114 to close the lumen of the profile 114 to aseptically seal the lumen of the profile 114. Suitable surface activation treatments include processing input energy to the end surface and/or at least partially within the lumen of the profile 114. In an embodiment, processing input energy is accomplished by wave irradiation, particle irradiation, or combination thereof. In an embodiment, the wave irradiation includes any wave irradiation envisioned, such as radio waves, microwaves, infrared, visible light, ultraviolet, x-rays, gamma radiation, or any combination thereof. In another embodiment, the particle irradiation includes alpha radiation, beta radiation, charged ions, neutron radiation, corona treatment, C-treatment, flame treatment, ion treatment, plasma treatment, or any combination thereof.

The sterile sealing apparatus 100 may generally comprise an operation chamber 102, a plasma generator 104, a mechanical motion module 106, and a control system 108. In some embodiments, the sterile sealing apparatus may also comprise one or more additional modules 110. The operation chamber 102 may generally comprise an enclosure that defines a substantially sealed, internal environment 112 where a sterile sealing operation of the profile 114 may occur. The plasma generator 104 may generally be configured to generate ionized particles through a plasma treatment (e.g., corona treatment, C-treatment, flame treatment, ion treatment, plasma treatment, or any combination thereof) within the operation chamber 102 that may selectively be applied to the end surface and/or at least partially within the lumen of the profile 114 to activate material on the end surface and/or within the lumen of the profile 114. The mechanical motion module 106 may generally be configured to manipulate the profile 114 to force the lumen of the profile 114 to close. The control system 108 may generally comprise a user interface 116 and a plurality of sensors 118, indicators, gauges, or a combination thereof to facilitate control, monitoring, and operation of the sterile sealing operation.

It will be appreciated that traditional sealing apparatuses that use high temperature methods cannot effectively seal thermoset elastomers, such as silicone elastomers. However, the sterile sealing apparatus 100 is configured to aseptically seal a wide range of materials. In some embodiments, the profile 114 may be formed from a polymeric material, such as a thermoplastic elastomer, a thermoset elastomer, or combination thereof. In some embodiments, the thermoplastic elastomer may comprise a polystyrene, a polyester, a silicone copolymer, a silicone thermoplastic vulcanizate, a copolyester, a polyamide, a fluoropolymer, a polyolefin, a polyether-ester copolymer, a thermoplastic urethane, a polyether amide block copolymer, a polyamide copolymer, a styrene block copolymer, a polycarbonate, a thermoplastic vulcanizate, an ionomer, a polyoxymethylene (POM), an acrylonitrile butadiene styrene (ABS), an acetal, an acrylic, a polyvinyl chloride (PVC), a blend, or any combination thereof. In some embodiments, the thermoset elastomer may comprise a silicone elastomer, a diene elastomer, a butyl rubber, a natural rubber, a polyurethane rubber, an ethylene propylene diene monomer rubber, an isoprene rubber, a nitrile rubber, a styrene butadiene rubber, a blend, or any combination thereof.

In some embodiments, the operation chamber 102 may comprise an enclosure that defines a substantially sealed, internal environment 112 that is separated from an external environment, such as a clean room 120 and/or ambient atmosphere 122 outside the clean room 120 and/or a structure, such as a medical facility. In some embodiments, the operation chamber 102 may be configured to at least partially receive the profile 114 to facilitate the sterile sealing operation. However, to maintain a sterile internal environment 112 within the operation chamber 102, the operation chamber 102 may be configured to maintain a fluid tight seal when the profile 114 is at least partially received within the operation chamber 102 and at least partially protrudes therefrom. As such, in some embodiments, the operation chamber 102 may function to confine a plasma or plasma treatment within the internal environment 112.

In some embodiments, the operation chamber 102 may comprise at least one transparent surface 124 through which the profile 114 is visible. In other embodiments, the operation chamber 102 may comprise multiple transparent surfaces 124 through which the profile 114 is visible. In yet other embodiments, the operation chamber 102 may be formed from a transparent material (e.g., acrylic, acrylic glass, plexiglass, polycarbonate, or a combination thereof) that allows observation of the profile 114 by an operator from all angles and/or sides of the operation chamber 102. These embodiments may allow an operator to observe the sterile sealing operation and/or inspect the final seal of the profile 114 for completion, quality, or a combination thereof. Further, in some embodiments, to protect the safety of an operator and/or integrity of the plasma treatment, the transparent surface(s) 124 may at least partially block ultraviolet light from entering or exiting the enclosure.

As stated, the operation chamber 102 may maintain a substantially sterile, internal environment 112 within the operation chamber 102. In some embodiments, this may be facilitated by a two-way ventilation system 126. In some embodiments, the ventilation system 126 may exchange and/or filter air within the internal environment 112 via a first exchange system 128. In some embodiments, the ventilation system 126 may exchange and/or filter air between the clean room 120 and the internal environment 112 via a second exchange system 130. Further, in some embodiments, the ventilation system 126 may exchange and/or filter air between the ambient atmosphere 122 and the internal environment 112 via a third exchange system 132. As such, the ventilation system 126 may comprise a filter, a catalytic converter, a radiative element, or a combination thereof that treats (e.g., filters, sterilizes, reduces ozone, temperature conditions, or combinations thereof) air received from the clean room 120 via the second exchange system 130 and that enters or exits the internal environment 112 of the operation chamber 102 through the first exchange system 128. Additionally, the ventilation system 126 may also comprise a filter, a catalytic converter, a radiative element, or a combination thereof that treats air received from ambient atmosphere 122 via the third exchange system 132 and that enters or exits the internal environment 112 of the operation chamber 102 through the first exchange system 128.

The plasma generator 104 may generally comprise a gas supply 134, a power supply 136, and at least one plasma head 138 and be configured to generate ionized particles through a plasma treatment (e.g., corona treatment, C-treatment, flame treatment, ion treatment, plasma treatment, or combinations thereof) within the operation chamber 102 that may selectively be applied to the end surface and/or at least partially within the lumen of the profile 114 to activate material on end surface and/or within the lumen of the profile 114. The gas supply 134 may be configured to provide a flow of one or more gases, such as an inert gas, an oxygen containing gas, a nitrogen containing gas, a fluorine containing gas, or any combination thereof. In some embodiments, the gas supply 134 may comprise an atmospheric air supply, a compressor, a compressed gas cylinder, an in-house gas line, an in-house compressed gas line, a fan, a turbo, or any combination thereof to produce the flow of gas. In some embodiments, the inert gas may comprise argon, neon, helium, or any combination thereof. In other embodiments, the oxygen containing gas may comprise atmospheric air, pure oxygen, alcohol, water vapor, or a combination thereof. In yet other embodiments, the nitrogen containing gas may comprise atmospheric air, pure nitrogen, ammonia, or a combination thereof. Still, in other embodiments, the fluorine containing gas may comprises sulfur hexafluoride ($SF_6$), trifluoromethane ($CHF_3$), tetrafluoromethane ($CF_4$), octafluorocyclobutane ($C_4F_8$), or a combination thereof.

The power supply 136 may generally be configured to ionize the flow of gas by imparting an electrical charge to the flow of gas to generate the plasma treatment. In some embodiments, the power supply 136 may be configured to provide an alternating current voltage of at least 110 VAC, at least 120 VAC, at least 220 VAC, or at least 240 VAC. However, in other embodiments, the power supply 136 may be configured to provide a direct current voltage of at least 6 VDC, at least 9 VDC, at least 12 VDC, at least 24 VDC, or at least 48 VDC.

The plasma treatment may be delivered to the at least one plasma head 138 disposed within the internal environment 112 of the operation chamber 102 through at least one supply line 137. The plasma head 138 may be disposed within the internal environment 112 of the operation chamber 102 and located within the operation chamber 102, such that the at least one plasma head 138 applies the plasma treatment to the end contact surface and/or at least partially within the lumen of the profile 114. Accordingly, applying the plasma treatment to the end surface and/or at least partially within the lumen of the profile 114 may comprise exposing or subjecting the end surface and/or the lumen of the profile 114 to the plasma treatment or delivering or directing the plasma treatment to contact or substantially envelope the end surface and/or at least partially penetrate the lumen of the profile 114. By applying the plasma treatment to the end surface and/or at least partially within the lumen of the profile 114, material at the end surface and/or at least partially within the lumen of the profile 114 may be activated for aseptically sealing the profile 114 when the profile 114 is manipulated to close the lumen of the profile 114 to aseptically seal the lumen of the profile 114.

In some embodiments, the plasma generator 104 may comprise a single plasma head 138 disposed within the internal environment 112 of the operation chamber 102. However, in some embodiments, the plasma generator 104 may comprise a plurality of plasma heads 138 disposed within the internal environment 112 of the operation chamber 102. In a particular embodiment, at least one plasma head 138 may be disposed axially adjacent to the end surface of the profile 114 within the operation chamber 102, such that the plasma head 138 may direct the plasma treatment to contact or substantially envelope the end surface and/or at least partially penetrate the lumen of the profile 114. In another particular embodiment, at least one plasma head 138 may be configured to sterilize the internal environment 112 within the operation chamber 102.

Once the material at the end surface and/or within the lumen of the profile 114 is activated, the mechanical motion module 106 may generally be configured to apply a force or pressure to and/or manipulate the profile 114 in a manner to close the lumen of the profile 114 to aseptically seal the lumen of the profile 114. Manipulating the profile 114 may include clamping, flattening, pinching, pressing, or otherwise squeezing the profile 114 radially to close the lumen of the profile 114. In some embodiments, the mechanical motion module 106 may be disposed at least partially within the operation chamber 102 or at least partially form a lower barrier or perimeter of the internal environment 112 of the operation chamber 102.

In some embodiments, the mechanical motion module 106 may comprise a cutting device 140. The cutting device 140 may generally be disposed in the internal environment 112 of the operation chamber 102. In some embodiments, the cutting device 140 may be configured to cut a piece of tubing placed in and/or through the operation chamber 102 to form the profile 114 and/or expose the end contact surface and the lumen of the profile 114. As such, a piece of tubing to be aseptically sealed may be placed into and/or through the operation chamber 102 and selectively cut by the cutting device 140 to form the profile 114 and expose the end surface and the lumen of the profile 114. Further, it will be appreciated that the plasma treatment may be applied to the piece of tubing prior to cutting the tubing with the cutting device 140, such that upon cutting the tubing, the end surface and the lumen of the profile 114 are immediately exposed to the plasma treatment. In some embodiments, the plasma treatment may be applied to the tubing prior to cutting the tubing for at least 1 second, at least 2 seconds, at least 3 seconds, at least 5 seconds, at least 10 seconds, or at least 15 seconds. In some embodiments, the cutting device 140 may comprise at least one blade, and the at least one blade may be heated, pre-sterilized, or a combination thereof. However, in some embodiments, the cutting device 140 may comprise a laser cutting system.

Figure 2:
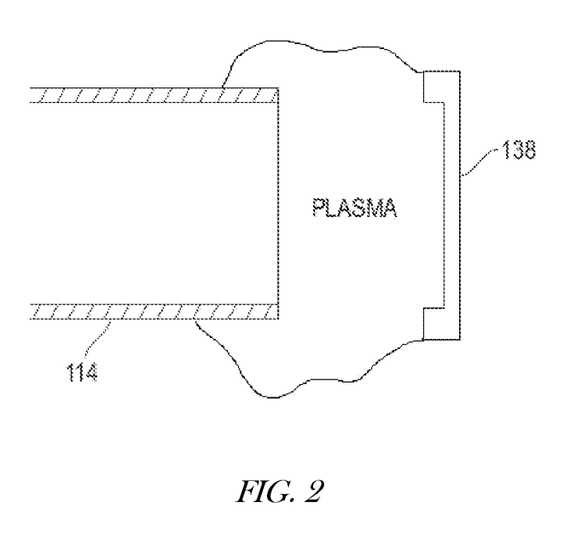
FIG. 2 shows a profile in an open position prior to sterile sealing.

FIG. 2 shows the profile 114 in an open position and subjected to the plasma treatment for sterile sealing. The plasma treatment may be applied before manipulation of the profile 114 by the mechanical motion module 106 to activate material on the end surface and/or within the lumen of the profile 114 for sealing and to further sterilize the lumen of the profile 114. In some embodiments, the plasma treatment may begin at least 1 second, at least 2 seconds, at least 3 seconds, at least 5 seconds, at least 10 seconds, at least 15 seconds at least 30 seconds, at least 45 seconds at least 60 seconds, at least 90 seconds, or at least 120 seconds before closing the profile 114.

Figure 3:
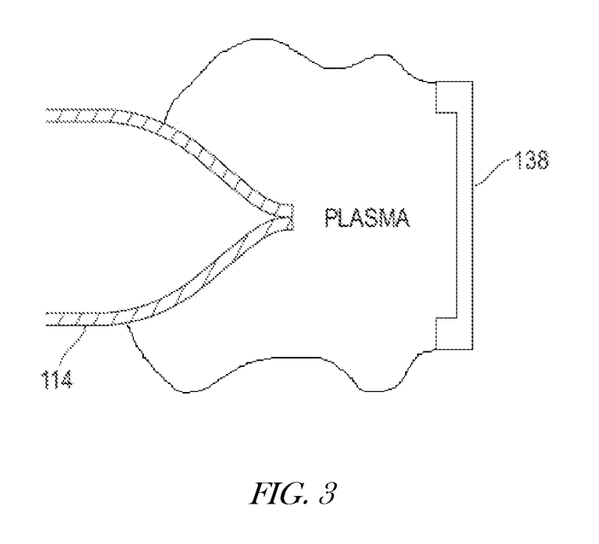
FIG. 3 shows a profile in a closed position after sterile sealing.
Figure 4:
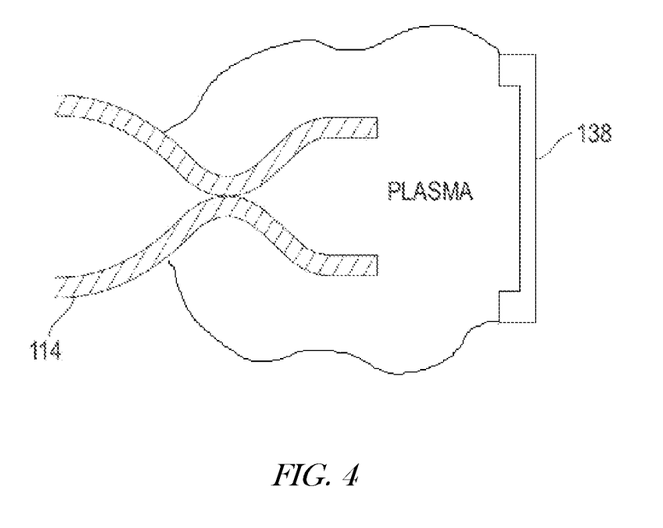
FIG. 4 shows a profile in another closed position after sterile sealing.

FIG. 3 shows the profile 114 in a closed position and subjected to the plasma treatment after sterile sealing. As shown in FIG. 3, the sterile seal may be formed at a distal end surface of the profile 114. FIG. 4 shows the profile 114 in another closed position and subjected to the plasma treatment after sterile sealing. As shown in FIG. 4, the sterile seal may be formed away from a distal end surface of the profile 114. Accordingly, the plasma treatment may continue after the profile 114 is closed and/or sealed to ensure a sterile connection, thereby forming an aseptically sealed profile 114. In some embodiments, the plasma treatment may continue for at least 1 second, at least 2 seconds, at least 3 seconds, at least 5 seconds, at least 10 seconds, at least 15 seconds at least 30 seconds, at least 45 seconds at least 60 seconds, at least 90 seconds, or at least 120 seconds after closing and/or sealing the profile 114.

Ensuring a sterile seal of the profile 114 may be the result of pretreating the internal environment 112 of the operation chamber 104 with the plasma treatment. Further, ensuring the sterile seal of the profile 114 may also be the result of continuing to apply the plasma treatment after the profile 114 is sealed. Accordingly, the plasma treatment provides an internal environment 112 of the operation chamber 102 with a sterile environment, wherein the sterile environment is defined by a reduction in the amount of living microorganisms within the internal environment 112 of the operation chamber by a level of at least $10^6$ after an exposure to the plasma treatment or plasma for at least 10 seconds, at least 15 seconds, at least 20 seconds, at least 25 seconds, at least 30 seconds or at least 60 seconds.

Furthermore, it will be appreciated that the sterile sealing process may be performed at various temperatures within the internal environment 112 of the operation chamber 102. For example, in some embodiments, the sterile sealing process may be performed at room temperature, such as that within the clean room 120. However, it will be appreciated that the sterile sealing process may be performed and configured to provide a sterile sealed connection at of the profile 114 at any temperature between about 10 degrees Celsius to 350 degrees Celsius.

Still referring to FIG. 1, the control system 108 may generally comprise a user interface 116 and a plurality of sensors 118, indicators, gauges, or a combination thereof to facilitate control, monitoring, and operation of the plasma generator 104, the mechanical motion module 106, and the sterile sealing process. The user interface 116 may generally comprise a display configured to display a temperature, a gas flow rate, a gas pressure, a gas detection level, a material of the profile 114, a plasma treatment progress level, a working cycle, a total number of working cycles, or a combination thereof. In a particular embodiment, the user interface 116 may comprise a material selection input for selecting properties a material of the profile 114. Furthermore, in some embodiments, the user interface 116 may comprise a warning system configured to alert an operator when an out of conformance condition exists. The user interface 116 may also be configured to automatically stop the plasma treatment when an out of conformance condition exists. Example out of conformance conditions include, but are not limited to a low temperature, a high temperature, a low pressure, a high pressure, a low gas flow rate, a high gas flow rate, a detection of a plasma byproduct, an invalid selection of a material, a leak in the operation chamber, or a combination thereof. When such conditions occur, the control system 108 may prevent opening and/or removal of the operation chamber 102. Further, the control system 108 may also prevent opening and/or removal of the operation chamber 102 during application of the plasma treatment.

The plurality of sensors 118, indicators, gauges, or combinations thereof may generally be configured to convey data (e.g., operational parameters) regarding the sterile sealing process to an operator and allow an operator to oversee the sterile sealing process. In some embodiments, the plurality of sensors 118 may comprise a temperature sensor, a gas flow rate sensor, a gas pressure sensor, a gas detection sensor, a plasma byproduct sensor, a tension sensor, or a combination thereof. Further, in some embodiments, the control system 108 may be configured to log or store data transmitted from the sensors 118 related to operation of the sterile sealing apparatus 100. This data may be used in troubleshooting and/or adjusting operational parameters of the components 102, 104, 106, 108 of the sterile sealing apparatus 100 or the sterile sealing process.

Furthermore, in some embodiments, the control system 108 may comprise at least one vision system and/or optical system (e.g., camera, inspection, video) configured to confirm successful closing of the lumen of the profile 114 and/or sealing of the profile 114. In some embodiments, the control system 108 may also comprise a marking system configured to mark the profile 114 via laser marking, ink marking, or any combination thereof that allows identification, verification, troubleshooting or any combination thereof of one or more characteristics of the sealed profile 114.

The sterile sealing apparatus 100 may be configured to form a sterile seal of the profile 114. The resulting sealed profile 114 may retain specific performance characteristics commensurate with an unmodified control bulk material of the sealed profile 114. Accordingly, in some embodiments, the control system 108 may be configured to conduct a burst test, a tension test, or a combination thereof of the sealed profile 114 to ensure a successful sterile sealing process. In some embodiments, the sealed profile 114 may comprise a burst pressure of at least 10%, at least 25%, at least 50%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 95%, or at least 100% or more of the burst pressure of an unmodified control bulk material of the profile 114. In an exemplary embodiment, a piece of 50 Durometer, ½ inch (1.27 cm) inner diameter, ¾ inch (1.905 cm) outer diameter tubing was aseptically sealed utilizing the sealing process described herein. The aseptic seal had a ¼ inch (0.635 cm) seal width. The 50 Durometer tubing burst under pressure prior to the aseptic seal bursting. In another exemplary embodiment, a piece of 65 Durometer, ½ inch (1.27 cm) inner diameter, ¾ inch (1.905 cm) outer diameter tubing was aseptically sealed utilizing the sealing process described herein. For the 65 Durometer tubing, the aseptic seal burst at about 46 psi (317.16 kPa), compared to the burst pressure of 51 psi (351.63 kPa) of the tubing itself. Thus, the sealing process disclosed herein is suitable for biopharmaceutical applications.

The sterile sealing apparatus 100 may generally be configured such that the operation chamber 102 and the mechanical motion module 106 are configured for mobile use and remotely coupled to the plasma generator 104 and/or the control system 108. Additionally, in some embodiments, the sterile sealing apparatus 100 may be a unitary apparatus mounted to a cart or other apparatus for mobile utility, in which the entire sterile sealing apparatus 100 may be moved or relocated.

Figure 5:
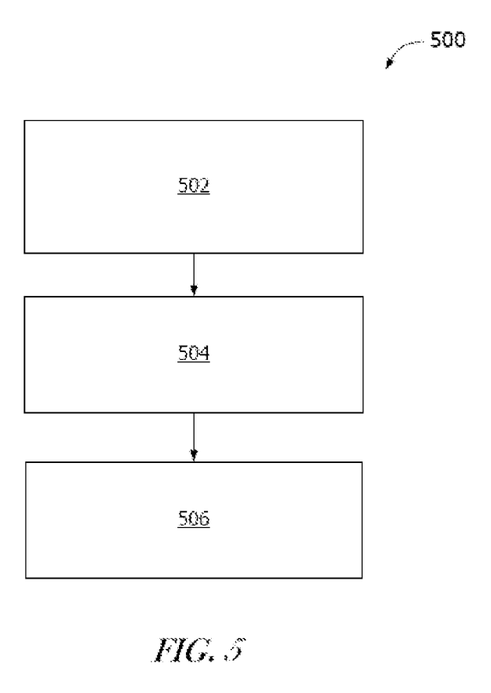
FIG. 5 is a flowchart of a method of operating a sterile sealing apparatus according to an embodiment of the disclosure.

Referring to FIG. 5, a flowchart of a method 500 of operating a sterile sealing apparatus 100 is shown according to an embodiment of the disclosure. The method 500 may begin at block 502 by generating a plasma treatment with a plasma generator 104. The method 500 may continue at block 504 by applying the plasma to an end surface and/or at least partially within a lumen of a profile 114 within an operation chamber 102. The method 500 may continue at block 506 by manipulating the profile 114 to close the lumen of the profile 114 to aseptically seal the lumen of the profile 114.

In some embodiments, the method 500 may comprise one or more of the following: ionizing a flow of gas comprising an inert gas, an oxygen containing gas, a nitrogen containing gas, a fluorine containing gas, or a combination thereof to generate the plasma treatment; sterilizing the internal environment 112 within the operation chamber 102 by applying the plasma treatment within the operation chamber 102; cutting a piece of tubing placed into and/or through the operation chamber 102 to form the profile 114; applying the plasma treatment to the profile 114 prior to cutting and/or closing the lumen of the profile 114, wherein the plasma treatment is applied to the profile 114 at least 1 second, at least 2 seconds, at least 3 seconds, at least 5 seconds, at least 10 seconds, at least 15 seconds at least 30 seconds, at least 45 seconds at least 60 seconds, at least 90 seconds, or at least 120 seconds before cutting the profile 114 and applying the plasma to the profile 114 after closing the lumen of the profile 114, wherein the plasma is applied to the profile 114 at least 1 second, at least 2 seconds, at least 3 seconds, at least 5 seconds, at least 10 seconds, at least 15 seconds at least 30 seconds, at least 45 seconds at least 60 seconds, at least 90 seconds, or at least 120 seconds after closing the lumen of the profile 114.

In some embodiments, the method 500 may also comprise one or more of the following: confirming successful closing and/or sealing of the lumen of the profile 114; monitoring a temperature, a gas flow rate, a gas pressure, a gas detection level, a material of the profile, a plasma treatment progress level, a working cycle, a total number of working cycles, or a combination thereof; displaying the temperature, the gas flow rate, the gas pressure, the gas detection level, the material of the profile 114, the plasma treatment progress level, the working cycle, the total number of working cycles, or a combination thereof on a user interface 116; alerting a user when an out of conformance condition exists; automatically stopping the plasma treatment when an out of conformance condition exists, wherein the out of conformance condition comprises a low temperature, a high temperature, a low pressure, a high pressure, a low gas flow rate, a high gas flow rate, a detection of a plasma byproduct, an invalid selection of a material, a leak in the operation chamber 102, or a combination thereof; storing data related to operation of the sterile sealing apparatus 100; conducting a burst test of the profile 114; and selecting a material of the profile 114 via the user interface 116.

In still other embodiments, the sealing apparatus may include one or more of the following items:

Embodiment 1. A sealing apparatus, comprising: an operation chamber; a plasma generator having at least one plasma head disposed within the operation chamber and in proximity to a profile within the operation chamber, wherein the plasma head is configured to apply a plasma treatment to the profile to activate material on an end surface of the profile, within a lumen of the profile, or combinations thereof; and a mechanical motion module configured to manipulate the profile to close the lumen of the profile to aseptically seal the profile.

Embodiment 2. A sterile sealing apparatus, comprising: an operation chamber; at least one cutting device disposed within the operation chamber and configured to cut a piece of tubing inserted into the operation chamber to form a profile; a plasma generator having at least one plasma head disposed within the operation chamber and in proximity to the profile within the operation chamber, wherein the plasma head is configured to apply a plasma treatment to the profile to activate material on an end surface of the profile, within a lumen of the profile, or combinations thereof; and a mechanical motion module configured to manipulate the profile to close the lumen of the profile to aseptically seal the profile.

Embodiment 3. The sterile sealing apparatus of any of Embodiments 1 to 2, wherein the profile is formed from a polymeric material.

Embodiment 4. The sterile sealing apparatus of Embodiment 3, wherein the profile is formed from a thermoplastic elastomer, a thermoset elastomer, or a combination thereof.

Embodiment 5. The sterile sealing apparatus of Embodiment 4, wherein the thermoplastic elastomer comprises a polystyrene, a polyester, a silicone copolymer, a silicone thermoplastic vulcanizate, a copolyester, a polyamide, a fluoropolymer, a polyolefin, a polyether-ester copolymer, a thermoplastic urethane, a polyether amide block copolymer, a polyamide copolymer, a styrene block copolymer, a polycarbonate, a thermoplastic vulcanizate, an ionomer, a polyoxymethylene (POM), an acrylonitrile butadiene styrene (ABS), an acetal, an acrylic, a polyvinyl chloride (PVC), a blend, or a combination thereof.

Embodiment 6. The sterile sealing apparatus of Embodiment 4, wherein the thermoset elastomer comprises a silicone elastomer, a diene elastomer, a butyl rubber, a natural rubber, a polyurethane rubber, an ethylene propylene diene monomer rubber, an isoprene rubber, a nitrile rubber, a styrene butadiene rubber, a blend, or a combination thereof.

Embodiment 7. The sterile sealing apparatus of any of Embodiments 1 to 6, wherein the operation chamber comprises an enclosure having at least one transparent surface through which the profile is visible.

Embodiment 8. The sterile sealing apparatus of Embodiment 7, wherein the operation chamber comprises an enclosure having multiple transparent surfaces through which the profile is visible.

Embodiment 9. The sterile sealing apparatus of any of Embodiments 7 and 8, wherein the transparent surface(s) at least partially blocks ultraviolet light from entering or exiting the enclosure.

Embodiment 10. The sterile sealing apparatus of any of Embodiments 1 to 9, wherein the operation chamber forms a substantially sealed environment.

Embodiment 11. The sterile sealing apparatus of Embodiment 10, wherein the operation chamber confines the plasma treatment within the substantially sealed environment.

Embodiment 12. The sterile sealing apparatus of Embodiment 11, wherein the operation chamber is prevented from opening or removal during application of the plasma treatment.

Embodiment 13. The sterile sealing apparatus of any of Embodiments 1 to 12, wherein the operation chamber comprises a ventilation system that provides a two-way air exchange with the operation chamber.

Embodiment 14. The sterile sealing apparatus of Embodiment 13, wherein the ventilation system comprises a filter, a catalytic converter, a radiative element, or a combination thereof that treats the atmospheric air prior to the air entering or exiting the operation chamber.

Embodiment 15. The sterile sealing apparatus of any of Embodiments 1 to 13, wherein the plasma generator comprises a gas supply and a power supply.

Embodiment 16. The sterile sealing apparatus of Embodiment 15, wherein the gas supply comprises an atmospheric air supply, a compressor, a compressed gas cylinder, an in-house gas line, an in-house compressed gas line, a fan, a turbo, or a combination thereof.

Embodiment 17. The sterile sealing apparatus of Embodiment 16, wherein the gas supply provides a flow of gas comprising an inert gas, an oxygen containing gas, a nitrogen containing gas, a fluorine containing gas, or a combination thereof.

Embodiment 18. The sterile sealing apparatus of Embodiment 17, wherein the inert gas comprises argon, neon, helium, or any combination thereof.

Embodiment 19. The sterile sealing apparatus of Embodiment 17, wherein the oxygen containing gas comprises atmospheric air, pure oxygen, alcohol, water vapor, or a combination thereof.

Embodiment 20. The sterile sealing apparatus of Embodiment 17, wherein the nitrogen containing gas comprises atmospheric air, pure nitrogen, ammonia, or a combination thereof.

Embodiment 21. The sterile sealing apparatus of Embodiment 17, wherein the fluorine containing gas comprises sulfur hexafluoride ($SF_6$), trifluoromethane ($CHF_3$), tetrafluoromethane ($CF_4$), octafluorocyclobutane ($C_4F_8$), or a combination thereof.

Embodiment 22. The sterile sealing apparatus of any of Embodiments 17 to 21, wherein the power supply ionizes the flow of gas through a corona treatment, a C-treatment, a plasma treatment, a flame treatment, or any combination thereof to generate the plasma treatment.

Embodiment 23. The sterile sealing apparatus of Embodiment 22, wherein the power supply provides at least 110 VAC, at least 120 VAC, at least 220 VAC, or at least 240 VAC.

Embodiment 24. The sterile sealing apparatus of Embodiment 22, wherein the power supply provides at least 6 VDC, at least 9 VDC, at least 12 VDC, at least 24 VDC, or at least 48 VDC.

Embodiment 25. The sterile sealing apparatus of any of Embodiments 1 to 24, wherein the plasma generator comprises a supply line coupled to the at least one plasma head.

Embodiment 26. The sterile sealing apparatus of any of Embodiments 1 to 25, further comprising: a plurality of plasma heads disposed within the operation chamber.

Embodiment 27. The sterile sealing apparatus of Embodiment 26, wherein at least one of the plurality of plasma heads is configured to sterilize the environment within the operation chamber.

Embodiment 28. The sterile sealing apparatus of Embodiment 1 or any of Embodiments 3 to 27, further comprising: a cutting device disposed in the operation chamber and configured to cut a piece of tubing inserted into the operation chamber to form the profile.

Embodiment 29. The sterile sealing apparatus of Embodiment 2 or 28, wherein the cutting device comprises at least one blade, a heated blade, a pre-sterilized blade, cutting device comprises a laser cutting system, or any combination thereof.

Embodiment 30. The sterile sealing apparatus of Embodiment 2 or any of Embodiments 28 to 29, wherein the plasma treatment is applied to the tubing prior to cutting the tubing to form the profile.

Embodiment 31. The sterile sealing apparatus of Embodiment 30, wherein the plasma treatment is applied to the tubing prior to cutting the tubing for at least 1 second, at least 2 seconds, at least 3 seconds, at least 5 seconds, at least 10 seconds, or at least 15 seconds.

Embodiment 32. The sterile sealing apparatus of any of Embodiments 1 to 31, wherein the mechanical motion module closes the profile at a distal end of the profile.

Embodiment 33. The sterile sealing apparatus of any of Embodiments 1 to 31, wherein the mechanical motion module closes the profile away from a distal end of the profile.

Embodiment 34. The sterile sealing apparatus of any of Embodiments 1 to 33, further comprising: a control system.

Embodiment 35. The sterile sealing apparatus of Embodiment 34, wherein the control system comprises a user interface and a plurality of sensors, indicators, gauges, or a combination thereof.

Embodiment 36. The sterile sealing apparatus of Embodiment 35, wherein the user interface comprises a display.

Embodiment 37. The sterile sealing apparatus of Embodiment 36, wherein the display is configured to display a temperature, a gas flow rate, a gas pressure, a gas detection level, a material of the profile, a plasma treatment progress level, a working cycle, a total number of working cycles, or a combination thereof.

Embodiment 38. The sterile sealing apparatus of Embodiment 37, wherein the user interface comprises a material selection input for selecting properties of a material of the profile.

Embodiment 39. The sterile sealing apparatus of Embodiment 37, wherein the user interface comprises a warning system configured to alert a user when an out of conformance condition exists.

Embodiment 40. The sterile sealing apparatus of Embodiment 39, wherein the user interface is configured to automatically stop the plasma treatment when an out of conformance condition exists.

Embodiment 41. The sterile sealing apparatus of Embodiment 40, wherein the out of conformance condition comprises a low temperature, a high temperature, a low pressure, a high pressure, a low gas flow rate, a high gas flow rate, a detection of a plasma byproduct, an invalid selection of a material, a leak in the operation chamber, or a combination thereof.

Embodiment 42. The sterile sealing apparatus of Embodiment 35, wherein the plurality of sensors comprises a temperature sensor, a gas flow rate sensor, a gas pressure sensor, a gas detection sensor, a plasma byproduct sensor, a tension sensor, or a combination thereof.

Embodiment 43. The sterile sealing apparatus of any of Embodiments 34 to 42, wherein the control system comprises at least one camera, optical system, vision system, or a combination thereof configured to confirm successful closing of the lumen of the profile, sealing of the profile, or a combination thereof.

Embodiment 44. The sterile sealing apparatus of any of Embodiments 34 to 43, wherein the control system is configured to conduct a burst test of the profile after the profile is sealed.

Embodiment 45. The sterile sealing apparatus of any of Embodiments 34 to 44, wherein the control system is configured to store data related to operation of the sterile sealing apparatus.

Embodiment 46. The sterile sealing apparatus of any of Embodiments 1 to 45, wherein the plasma treatment occurs between 10 degrees Celsius to 350 degrees Celsius.

Embodiment 47. The sterile sealing apparatus of any of Embodiments 1 to 46, wherein the plasma treatment begins prior to manipulating the profile.

Embodiment 48. The sterile sealing apparatus of Embodiment 47, wherein the plasma treatment begins at least 1 second, at least 2 seconds, at least 3 seconds, at least 5 seconds, at least 10 seconds, at least 15 seconds at least 30 seconds, at least 45 seconds at least 60 seconds, at least 90 seconds, or at least 120 seconds before manipulating the profile.

Embodiment 49. The sterile sealing apparatus of any of Embodiments 1 to 48, wherein the plasma treatment continues after the profile is sealed.

Embodiment 50. The sterile sealing apparatus of Embodiment 49, wherein the plasma treatment continues for at least 1 second, at least 2 seconds, at least 3 seconds, at least 5 seconds, at least 10 seconds, at least 15 seconds, at least 30 seconds, at least 45 seconds, at least 60 seconds, at least 90 seconds, or at least 120 seconds after the profile is sealed.

Embodiment 51. The sterile sealing apparatus of any of Embodiments 1 to 50, wherein an aseptic seal of the profile comprises a burst pressure of at least 10%, at least 25%, at least 50%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 95%, or at least 100% of the burst pressure of an unmodified control bulk material of the profile.

Embodiment 52. A method of operating a sterile sealing apparatus, comprising: generating a plasma treatment with a plasma generator; applying the plasma treatment to an end surface of a profile, within a lumen of the profile, or a combination thereof within an operation chamber; and manipulating the profile to close the lumen of the profile to aseptically seal the profile.

Embodiment 53. The method of Embodiment 52, further comprising: cutting a piece of tubing inserted into the operation chamber to form the profile.

Embodiment 54. The method of Embodiment 53, further comprising: applying the plasma treatment to the tubing prior to cutting the tubing to form the profile.

Embodiment 55. The method of Embodiment 54, wherein the plasma treatment is applied to the tubing prior to cutting the tubing for at least 1 second, at least 2 seconds, at least 3 seconds, at least 5 seconds, at least 10 seconds, or at least 15 seconds.

Embodiment 56. The method of any of Embodiments 52 to 55, further comprising: ionizing a flow of gas comprising an inert gas, an oxygen containing gas, a nitrogen containing gas, a fluorine containing gas, or a combination thereof through a corona treatment, a C-treatment, a plasma treatment, a flame treatment, or any combination thereof to generate the plasma treatment.

Embodiment 57. The method of any of Embodiments 52 to 56, further comprising: sterilizing the environment within the operation chamber by applying the plasma treatment within the operation chamber.

Embodiment 58. The method of any of Embodiments 52 to 57, wherein the plasma treatment is applied within the operation chamber by at least one plasma head disposed within the operation chamber.

Embodiment 59. The method of Embodiment 58, further comprising: applying the plasma treatment to the profile prior to manipulating the profile.

Embodiment 60. The method of Embodiment 59, wherein the plasma treatment is applied to the profile at least 1 second, at least 2 seconds, at least 3 seconds, at least 5 seconds, at least 10 seconds, at least 15 seconds at least 30 seconds, at least 45 seconds at least 60 seconds, at least 90 seconds, or at least 120 seconds prior to manipulating the profile.

Embodiment 61. The method of any of Embodiments 52 to 60, further comprising: applying the plasma treatment to the profile after the profile is sealed.

Embodiment 62. The method of Embodiment 61, wherein the plasma treatment is applied to the profile at least 1 second, at least 2 seconds, at least 3 seconds, at least 5 seconds, at least 10 seconds, at least 15 seconds at least 30 seconds, at least 45 seconds at least 60 seconds, at least 90 seconds, or at least 120 seconds after the profile is sealed.

Embodiment 63. The method of any of Embodiments 52 to 62, further comprising: confirming successful closing of the lumen of the profile, sealing of the profile, or a combination thereof via a camera system.

Embodiment 64. The method of any of Embodiments 52 to 63, wherein the profile is sealed at a distal end of the profile.

Embodiment 65. The method of any of Embodiments 52 to 63, wherein the profile is sealed away from a distal end of the profile.

Embodiment 66. The method of any of Embodiments 52 to 65, further comprising: monitoring a temperature, a gas flow rate, a gas pressure, a gas detection level, a material of the profile, a plasma treatment progress level, a working cycle, a total number of working cycles, or a combination thereof.

Embodiment 67. The method of Embodiment 66, further comprising: displaying the temperature, the gas flow rate, the gas pressure, the gas detection level, the material of the profile, the plasma treatment progress level, the working cycle, the total number of working cycles, or a combination thereof on a user interface associated with a control system.

Embodiment 68. The method of any of Embodiments 66 to 67, further comprising: alerting a user when an out of conformance condition exists.

Embodiment 69. The method of Embodiment 68, further comprising: automatically stopping the plasma treatment when an out of conformance condition exists.

Embodiment 70. The method of Embodiment 69, wherein the out of conformance condition comprises a low temperature, a high temperature, a low pressure, a high pressure, a low gas flow rate, a high gas flow rate, a detection of a plasma byproduct, an invalid selection of a material, a leak in the operation chamber, or a combination thereof.

Embodiment 71. The method of any of Embodiments 66 to 70, further comprising: storing data related to operation of the sterile sealing apparatus.

Embodiment 72. The method of Embodiment 67, further comprising: selecting a material of the profile via the user interface.

Embodiment 73. The method of Embodiment 72, wherein the profile is formed from a polymeric material.

Embodiment 74. The method of Embodiment 73, wherein the profile is formed from a thermoplastic elastomer, a thermoset elastomer, or a combination thereof.

Embodiment 75. The method of Embodiment 74, wherein the thermoplastic elastomer comprises a polystyrene, a polyester, a silicone copolymer, a silicone thermoplastic vulcanizate, a copolyester, a polyamide, a fluoropolymer, a polyolefin, a polyether-ester copolymer, a thermoplastic urethane, a polyether amide block copolymer, a polyamide copolymer, a styrene block copolymer, a polycarbonate, a thermoplastic vulcanizate, an ionomer, a polyoxymethylene (POM), an acrylonitrile butadiene styrene (ABS), an acetal, an acrylic, a polyvinyl chloride (PVC), a blend, or combination thereof.

Embodiment 76. The method of Embodiment 74, wherein the thermoset elastomer comprises a silicone elastomer, a diene elastomer, a butyl rubber, a natural rubber, a polyurethane rubber, an ethylene propylene diene monomer rubber, an isoprene rubber, a nitrile rubber, a styrene butadiene rubber, a blend, or combination thereof.

Embodiment 77. The method of any of Embodiments 52 to 76, further comprising: confirming successful closing of the lumen of the profile, sealing of the profile, or a combination thereof utilizing at least one camera, optical system, vision system, or a combination thereof associated with a control system.

Embodiment 78. The method of any of Embodiments 52 to 77, further comprising: conducting a burst test of the profile after the profile is sealed.

Embodiment 79. The method of Embodiment 78, wherein an aseptic seal of the profile comprises a burst pressure of at least 10%, at least 25%, at least 50%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 95%, or at least 100% of the burst pressure of an unmodified control bulk material of the profile.

Embodiment 80. The sterile sealing apparatus of any of Embodiments 1 to 51 or the method of any of Embodiments 52 to 79, wherein applying the plasma treatment provides an interior environment of the operation chamber with a sterile environment, wherein the sterile environment is defined by reduction in an amount of living microorganisms within the interior environment of the operation chamber by a level of at least $10^6$ after an exposure to the plasma treatment for at least 10 seconds, at least 15 seconds, at least 20 seconds, at least 25 seconds, or at least 30 seconds.

Embodiment 81. The sterile sealing apparatus of any of Embodiments 1 to 51 or the method of any of Embodiments 52 to 80, wherein the sterile sealing apparatus comprises a unitary apparatus that is configured for mobile utility.

This written description uses examples to disclose the embodiments, including the best mode, and also to enable those of ordinary skill in the art to make and use the invention. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A sealing apparatus, comprising:
   an operation chamber;
   a plasma generator having at least one plasma head disposed within the operation chamber and in proximity to a profile comprising a lumen within the operation chamber, wherein the plasma head is configured to apply a plasma treatment to the profile to activate material on an end surface of the profile, within the lumen of the profile, or combinations thereof;
   wherein the profile is manipulated to close the lumen of the profile to aseptically seal the profile; and
   a cutting device comprising a blade or laser cutting system and configured to cut a piece of tubing inserted into the operation chamber to form the profile, wherein the plasma treatment is applied to the piece of tubing prior to cutting the piece of tubing to form the profile, wherein the profile comprises a thermoset elastomer.

2. The sealing apparatus of claim 1, wherein the profile is formed from: a thermoplastic elastomer comprising a polystyrene, a polyester, a silicone copolymer, a silicone thermoplastic vulcanizate, a copolyester, a polyamide, a fluoropolymer, a polyolefin, a polyether-ester copolymer, a thermoplastic urethane, a polyether amide block copolymer, a polyamide copolymer, a styrene block copolymer, a polycarbonate, a thermoplastic vulcanizate, an ionomer, a polyoxymethylene (POM), an acrylonitrile butadiene styrene (ABS), an acetal, an acrylic, a polyvinyl chloride (PVC), a blend, or a combination thereof, a silicone elastomer, a diene elastomer, a butyl rubber, a natural rubber, a polyurethane rubber, an ethylene propylene diene monomer rubber, an isoprene rubber, a nitrile rubber, a styrene butadiene rubber, a blend, or a combination thereof.

3. The sealing apparatus of claim 1, wherein the operation chamber comprises an enclosure having at least one transparent surface through which the profile is visible.

4. The sealing apparatus of claim 1, wherein the operation chamber forms an environment having a fluid tight seal when the profile is at least partially received within the operation chamber.

5. The sealing apparatus of claim 4, wherein the operation chamber confines the plasma treatment within the environment.

6. The sealing apparatus of claim 1, wherein the plasma generator comprises a gas supply, a power supply, and at least one supply line coupled to the at least one plasma head.

7. The sealing apparatus of claim 6, wherein the gas supply comprises an atmospheric air supply, a compressor, a compressed gas cylinder, an in-house gas line, an in-house compressed gas line, a fan, a turbo, or a combination thereof, and wherein the gas supply provides a flow of gas comprising an inert gas, an oxygen containing gas, a nitrogen containing gas, a fluorine containing gas, or a combination thereof.

8. The sealing apparatus of claim 7, wherein the power supply ionizes the flow of gas through a corona treatment, a C-treatment, a plasma treatment, a flame treatment, or any combination thereof to generate the plasma treatment.

9. The sealing apparatus of claim 8, wherein the power supply provides at least 110 VAC, at least 120 VAC, at least 220 VAC, or at least 240 VAC, or at least 6 VDC, at least 9 VDC, at least 12 VDC, at least 24 VDC, or at least 48 VDC.

10. The sealing apparatus of claim 1, wherein the at least one plasma head is configured to sterilize the environment within the operation chamber.

11. The sealing apparatus of claim 10, wherein the environment is defined as sterilized by reduction in an amount of living microorganisms within an interior environment of the operation chamber by a level of at least $10^6$ after an exposure to the plasma treatment for at least 10 seconds, at least 15 seconds, at least 20 seconds, at least 25 seconds, or at least 30 seconds.

12. The sealing apparatus of claim 1, wherein the profile is manipulated to close at a distal end of the profile.

13. The sealing apparatus of claim 1, wherein the profile is manipulated to close at a location that is away from a distal end of the profile.

14. The sealing apparatus of claim 1, wherein the plasma treatment begins prior to manipulating the profile, continues after the profile is sealed, or a combination thereof.

15. The sealing apparatus of claim 1, further comprising: a control system comprising a user interface and a plurality of sensors, indicators, gauges or a combination thereof.

16. The sealing apparatus of claim 15, wherein the control system comprises at least one camera, optical system, vision system, or a combination thereof configured to confirm successful closing of the lumen of the profile, sealing of the profile, or a combination thereof.

17. The sealing apparatus of claim 16, wherein the control system is configured to conduct a burst test of the profile after the profile is sealed.

18. The sealing apparatus of claim 16, wherein an aseptic seal of the profile comprises a burst pressure of at least 10%, at least 25%, at least 50%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 95%, or at least 100% of a burst pressure of an unmodified control bulk material of the profile.

* * * * *